US006288253B1

United States Patent
Manzer et al.

(10) Patent No.: US 6,288,253 B1
(45) Date of Patent: *Sep. 11, 2001

(54) SUPPORTED DENDRIMER CATALYST

(75) Inventors: Leo E. Manzer, Wilmington, DE (US); Prabhat Arya, Orleans (CA); Howard Alper; Sheila Christine Bourque, both of Ottawa (CA); Gary Jefferson, East Yorkshire (GB)

(73) Assignees: DuPont Canada Inc.; National Research Council; The University of Ottawa, all of Ontario (CA)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/350,705

(22) Filed: Jul. 9, 1999

Related U.S. Application Data

(60) Provisional application No. 60/092,473, filed on Jul. 10, 1998.

(51) Int. Cl.[7] .................................................. C07F 7/08
(52) U.S. Cl. .................. 556/9; 556/12; 556/136; 556/19; 556/20; 556/21; 556/413; 556/438; 502/150; 502/152; 502/158; 549/3; 560/55; 560/64; 585/25
(58) Field of Search .................. 502/150, 152, 502/158; 556/9, 12, 136, 413, 438, 19, 20, 21; 549/3; 560/64, 55; 585/25

(56) References Cited

U.S. PATENT DOCUMENTS

| | | |
|---|---|---|
| 4,507,466 | 3/1985 | Tomalia et al. . |
| 4,769,498 | 9/1988 | Billig et al. . |
| 5,969,073 | 10/1999 | Seyferth et al. . |
| 6,057,258 * | 5/2000 | Spitz et al. ............................ 502/152 |
| 6,077,806 * | 6/2000 | Cribbs et al. ................... 502/158 X |

OTHER PUBLICATIONS

Reetz, et al.–"Synthesis and Catalytic Activity of Dendritic Diphosphane Metal Complexes", Angew.Chem.Int.Ed.English (1997), pp. 1526–1527.

de Graaf, et al–"Dimethyl (N,N,N', N'–tetramethylethanediamine) palladium (II) and Dimethyl[1,2–bis(dimethylphosphino)ethane] palladium (II): Syntheses, X–ray Crystal Structures, and Thermolysis, Oxidative–Addition, and Ligand–Exchange Reactions", Organometallics, 8 pages 2907–2917, 1989.

de Meijere, et al–"Fine Feathers Make Fine Birds: The Heck Reaction in Modern Garb", Angew.Chem.Int.Ed.Engl. 33 (1994) pp. 2379–2411.

Zeng, et al–"Dendrimers in Supramolecular Chemistry: From Molecular Recognition to Self–Assembly", Chem.Rev. 1997 (1997) pp. 1681–1712.

Tomalia, et al–"Starburst Dendrimers: Molecular–Level Control of Size, Shape, Surface Chemistry, Topology, and Flexibility From Atoms to Macroscopic Matter", Angew.Chem.Int.Ed.Engl. 29 (1990) pp. 138–175.

Bourque, et al–"The Catalytic Activity of a Heterogeneous Dendritic Diphosphine Rhodium Complex", CSC98 Scientific Program published abstract fro the 81 Canadian Society for Chemistry and Exhibition (1998).

Miedaner, et al–"Electrochemical Reduction of $CO_2$ Catalyzed by Small Organophosphine Dendrimers Containing Palladium", Inorg.Chem. 33 (1994), pp. 5482–5490.

Liu, et al.–"pH–Switchable, Ultrathin Permselective Membranes Prepared From Multilayer Polymer Composites", J.Am.Chem.Soc. 119, (1977), pp. 8720–8721.

Knapen et al–"Homogenous Catalysts Based on Silane Dendrimers Functionalyzed with Arylnickel (II) Complexes" Letters to Nature vol. 372 (Dec. 15, 1994), pp. 659–663.

Liu, et al–"Multilayer Dendrimer–Polyanhydride Composite Films on Glass, Silicon, and Gold Wafers", .Angew.Chem.Int.Ed.Engl.19, (1997) pp. 2114–2116.

* cited by examiner

Primary Examiner—Paul F. Shaver
(74) Attorney, Agent, or Firm—Connolly Bove Lodge & Hutz LLP

(57) ABSTRACT

Dendrimers were directly and covalently attached to solid supports via siloxy bonds. After complexation with transition metals, the dendrimers were used as catalysts. The supported dendrimers were stable and easily separated from the reaction mixture.

26 Claims, No Drawings

SUPPORTED DENDRIMER CATALYST

FIELD OF INVENTION

This application claims the benefit of U.S. Provisional Application No. 60/092,473 filed on Jul. 10, 1998.

The invention relates to a novel method of supporting dendrimers on a solid support, and their use as catalysts.

BACKGROUND

Dendrimers, also known as arbolols, cascade molecules, dendritic polymers, or starburst polymers, have been attracting recent attention because of their unique structure and properties. The name comes from the Greek word for tree, in reference to their branch-like structure. They are a type of 3-dimensional, hyperbranched polymer, but differ in their ability to be prepared in a highly controlled, stepwise manner with narrow molecular weight distributions, many with no variation at all in weight. Dendrimers have a central core and an outer "surface" consisting of a high number of terminal groups which can be functionalized to provide the desired properties.

There are two main strategies for synthesizing dendrimers. In the divergent approach, the molecules are built from the central core out to the periphery. The convergent approach builds the molecule from the outer periphery towards the inner core. The divergent approach is outlined below.

The dendrimer starts with a core having at least two functional end groups capable of further reaction. Monomer units, having at least three functional end groups, are added in cycles to the core via one functional end group each, building a dendrimer framework. A monomer having three such end groups is considered to have a branch multiplicity of 2, indicating that two further monomers can be added to the framework on each existing branch. Each successive cycle is called a generation. In each generation a set number of monomer units are added to the functional end groups of the dendrimer framework, leading to a series of layers. This number is an exact multiple of the multiplicity. These cycles continue until the desired number of generations are added.

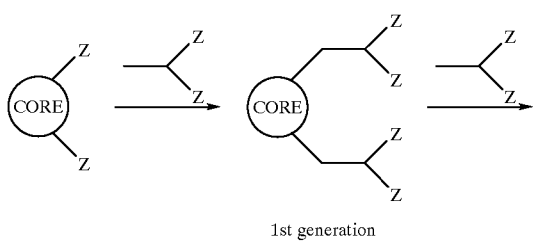

1st generation

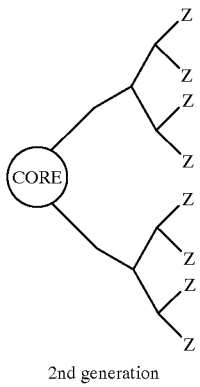

2nd generation

A pioneer in this type of chemistry is Donald Tomalia, who wrote an early review summarizing the history of area (D. Tomalia, et al, Angew. Chem. Int. Ed. Engl., 29 (1990), 138–75). Recent developments were reviewed in 1997 (F. Zeng and S. Zimmerman, Chem. Rev., 97 (1990), 1681–1712).

Liu, et al (Angew. Chem. Int. Ed. Engl., 36 (1997), 2114–16, and J. Am. Chem. Soc. 119, (1997), 8720–21) describe a dendrimer covalently attached to a solid support. However, the dendrimer is not attached directly to the support but is attached to reactive sites on an intervening randomly dispersed polymer layer.

One of the many potential uses of dendrimers has been in catalysis. Metals can be attached to the surface of the dendrimers by complexation with appropriate functional groups. They combine the advantages of homogenous catalysis with heterogeneous catalysis since they have a specific number of structurally defined, catalytically active metal centers as in traditional homogenous catalysis, as well the ability for easily separation from the reaction mixture and reuse as in heterogeneous catalysis. Miedaner, et al. (Inorg. Chem., 33 (1990), 5482–5490), Knapen, et al. (Nature, 372 (1994), 659–663), and Reetz et al. (Angew. Chem. Int. Ed. Engl., 36 (1997), 1526–1528) all used small dendrimers complexed with Pd and Ni compounds as homogenous catalysts. The dendrimers were separated after reaction by precipitation and filtration. Recycling of the used catalysts was suggested but not demonstrated.

A published abstract (http://www.sfu.ca/csc98/program/00000383.htm) for the 81st Canadian Society for Chemistry Conference and Exhibition stated that a version of Tomalia's dendrimer complexed to $[Rh(CO)_2Cl]_2$ was used as a catalyst for hydroformylation. The paper was withdrawn before presentation.

A need exists for a method to prepare true heterogeneous dendrimer catalysts that are efficient and can be easily removed from reaction mixtures without an added precipitation step, but can also be recycled and used multiple times.

SUMMARY OF THE INVENTION

In accordance with the present invention, a supported dendrimer composition has been found comprising a siloxy core and branches emanating from the core, wherein said core is directly and covalently bonded to a solid support. The solid support is selected from the group consisting of $SiO_2$, $TiO_2$, $Al_2O_3$, $ZrO_2$, clays, zeolites, modified carbons, and organic resins. Preferably, the supported dendrimer composition core and branches are of the formula $$Si(O)_m(OH)_{3-m}[ZN](AB)_g(T)_{2g}$$

wherein:
  Z is selected from the group consisting of optionally substituted C2–C12 straight chain or branched alkyl chain, cycloalkyl group, and aryl;
  A is —(CHR$_3$)CHR$_4$Y—;
  Y is selected from the group consisting of —C(O)NH—, —P(O)(OR$_5$)NH—, and —C(N)NH—;
  B is —R$_6$NH—;
  T is selected from the group consisting of H, alkyl, —(CR$_8$R$_9$)$_y$N$_2$, —(CR$_8$R$_9$)$_y$P(R$_{10}$)$_2$, and —(CR$_8$R$_9$)$_y$P(NH)$_2$,
  R$_3$, R$_4$, R$_5$, R$_8$, and R$_9$ are independently selected from the group consisting of hydrogen, alkyl or aryl;
  R$_6$ is selected from the group consisting of optionally substituted C2–C12 straight chain or branched alkyl chain, cycloalkyl group, and aryl;
  R$_{10}$ is selected from the group consisting of hydrogen, alkyl, aryl, alkoxy and aryloxy;
  m=0–3;
  y=2–12; and $$g = \sum_{1}^{G} 2^G$$

where G=number of generations in the dendrimer.

More preferably, the solid support is SiO$_2$, Z is —(CH$_2$)$_3$—, A is —(CH$_2$)$_2$C(O)NH—, B is —(CH$_2$)$_2$N—, and T is —(CH$_2$)$_2$NH$_2$. The supported dendrimer composition can optionally be complexed at T with a transition metal, preferably Rh.

The invention also provides a process for the preparation of a dendrimer composition supported on a solid support comprising the steps of:
  a. directly attaching a siloxy core group to the solid support by covalent bonding between at least one oxygen on the siloxy group and the surface of the solid support;
  b. directly attaching a linker group to the core group, wherein the linker molecule contains at least two reactive functional groups; and
  c. constructing the arms of the dendrimer utilizing the core group as the starting point of the dendrimer.

Preferably, the supported dendrimer prepared in the above process is composed of core and branches of the formula

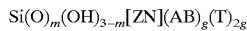

wherein:
  Z is selected from the group consisting of optionally substituted C2–C12 straight chain or branched alkyl chain, cycloalkyl group, and aryl;
  A is —(CHR$_3$)CHR$_4$Y—;
  Y is selected from the group consisting of —C(O)NH—, —P(O)(OR$_5$)NH—, and —C(N)NH—;
  B is —R$_6$NH—;
  T is selected from the group consisting of H, alkyl, —(CR$_8$R$_9$)$_y$NH$_2$, —(CR$_8$R$_9$)$_y$P(R$_{10}$)$_2$, and —(CR$_8$R$_9$)$_y$P(NH)$_2$,
  R$_3$, R$_4$, R$_5$, R$_8$, and R$_9$ are independently selected from the group consisting of hydrogen, alkyl or aryl;
  R$_6$ is selected from the group consisting of optionally substituted C2–C12 straight chain or branched alkyl chain, cycloalkyl group, and aryl;
  R$_{10}$ is selected from the group consisting of hydrogen, alkyl, aryl, alkoxy and aryloxy;
  m=0–3;
  y=2–12; and $$g = \sum_{1}^{G} 2^G$$

where G=number of generations in the dendrimer.

More preferably, the solid support is SiO$_2$, Z is —(CH$_2$)$_3$—, A is —(CH$_2$)$_2$C(O)NH—, B is —(CH$_2$)$_2$N—, and T is —(CH$_2$)$_2$NH$_2$. The supported dendrimer composition can optionally be complexed at T with a transition metal, preferably Rh.

The supported dendrimer composition may be used for a hydroformylation process comprising reacting an ethylenically unsaturated compound with a source of CO and H$_2$ in the presence of a supported catalyst. Preferably, the supported dendrimer used in the hydroformylation process is composed of core and branches of the formula

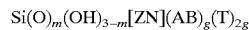

wherein:
  Z is selected from the group consisting of optionally substituted C2–C12 straight chain or branched alkyl chain, cycloalkyl group, and aryl;
  A is —(CHR$_3$)CHR$_4$Y—;
  Y is selected from the group consisting of —C(O)NH—, —P(O)(OR$_5$)NH—, and —CN)NH—;
  B is —R$_6$NH—;
  T is selected from the group consisting of H, alkyl, —(CR$_8$R$_9$)$_y$NH$_2$, —(CR$_8$R$_9$)$_y$P(R$_{10}$)$_2$, and —(CR$_8$R$_9$)$_y$P(NH)$_2$,
  R$_3$, R$_4$, R$_5$, R$_8$, and R$_9$ are independently selected from the group consisting of hydrogen, alkyl or aryl;
  R$_6$ is selected from the group consisting of optionally substituted C2–C12 straight chain or branched alkyl chain, cycloalkyl group, and aryl;
  R$_{10}$ is selected from the group consisting of hydrogen, alkyl, aryl, alkoxy and aryloxy;
  m=0–3;
  y=2–12; and $$g = \sum_{1}^{G} 2^G$$

where G=number of generations in the dendrimer.

More preferably, the solid support is SiO$_2$, Z is —(CH$_2$)$_3$—, A is —(CH$_2$)$_2$C(O)NH—, B is —(CH$_2$)$_2$N—, and T is —(CH$_2$)$_2$NH$_2$. The supported dendrimer composition can optionally be complexed at T with a transition metal, preferably Rh.

The invention also provides for a Pd supported dendrimer composition that may be used for carbon—carbon bond formation comprising contacting an unsaturated halide of the formula R'-X wherein X is a halogen and R' is selected from the group consisting of aryl, alkenyl and alkynyl, with a vinylic compound of the formula H$_2$C=CH-R" wherein R" is selected from the group consisting of hydrogen, hydrocarbyl, substituted hydrocarbyl, hydrocarbylamino, alkoxy, aryloxy, heterocyclic, carboxy and carboxyester, to produce a compound of the formula R'—CH=CH—R" in the presence of a supported catalyst wherein the supported catalyst comprises a supported dendrimer composition comprising a siloxy core and branches emanating from the core, wherein said core is directly and covalently bonded to a solid. Optionally the reaction may be performed intramolecularly resulting in a cyclic compound where R' and R" together form a ring.

A preferred version of the Pd catalyst is where the solid support is selected from the group consisting of $SiO_2$, $TiO_2$, $Al_2O_3$, $ZrO_2$, clays, zeolites, modified carbons, and organic resins and the supported dendrimer composition is of the formula

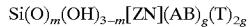

$$Si(O)_m(OH)_{3-m}[ZN](AB)_g(T)_{2g}$$

wherein:

Z is selected from the group consisting of optionally substituted C2–C12 straight chain or branched alkyl chain, cycloalkyl group, and aryl;

A is —$(CHR_3)CHR_4Y$—;

Y is selected from the group consisting of —C(O)NH—, —P(O)(OR$_5$)NH—, and —C(N)NH—;

B is —$R_6NH$—;

T is selected from the group consisting of H, alkyl, —$(CR_8R_9)_yNH_2$, —$(CR_8R_9)_yP(R_{10})_2$, and —$(CR_8R_9)_yP(NH)_2$, $R_3$, $R_4$, $R_5$, $R_8$, and $R_9$ are independently selected from the group consisting of hydrogen, alkyl or aryl;

$R_6$ is selected from the group consisting of optionally substituted C2–C12 straight chain or branched alkyl chain, cycloalkyl group, and aryl;

$R_{10}$ is selected from the group consisting of hydrogen, alkyl, aryl, alkoxy and aryloxy;

m=0–3;

y=2–12; and $$g = \sum_{1}^{G} 2^G$$

where G=number of generations in the dendrimer.

More preferably the solid support is $SiO_2$, Z is —$(CH_2)_3$—, A is —$(CH_2)_2C(O)NH$—, B is —$(CH_2)_2N$—, and T is —$(CH_2)P(C_6H_5)_2$, and the supported dendrimer composition is complexed at T with Pd. Most preferably R' is selected from the group consisting of aryl and substituted aryl, and R" is selected from the group consisting of carboxy, carboxy ester, aryl and substituted aryl.

In another aspect of the invention, a process for the preparation of a supported dendrimer composition, wherein a siloxy core is directly and covalently bounded to a solid support comprising the steps of:

a. constructing the arms of the dendrimer utilizing a core group as the starting point of the dendrimer, wherein the core group is attached via a linker group to a siloxy core group; and b. directly attaching the siloxy group to the solid support via covalent bonding between at least one oxygen on the siloxy group and the surface of the solid support.

DETAILED DESCRIPTION OF THE INVENTION

The dendrimers of the invention are defined as molecular constructions having a branched structure in which polymeric arms are attached to a core, and extend radially away from it. The arms may be linear, simple or star dendrimers, or may themselves be further branched, or even comprise closed branched structures such as loops. The arms are composed of segments, which are defined as any linear section between branch points (or extending out from a single branch point in the case of a linear or unbranched arm). Together the arms comprise the major part of the mass of the polymer and dominate its properties.

Dendrimers may typically be distinguished from other types of branched polymers in that:

(a) The arms are long with respect to the size of the core. The ratio of the mean molecular weight of individual arms to the molecular weight of the core should be greater than or equal to one.

(b) The arms are relatively closely spaced on the core. The mean number of polymer repeat units in the case of polymeric cores (or backbone atoms where the core is not polymeric), per branch point on the core should be less than or equal to 25, preferably between 1 to 20 and most preferably between 1 and 4.

(c) The material is relatively highly branched. The mean number of polymer repeat units in the arm segments (i.e., between branch points) should not exceed 500, preferably being less than 150, most preferably less than 50, preferably more than 4, more preferably more than 10 and most preferably more than 20.

There is no implication of regularity of structure beyond the definitions above; the arms may differ in length, and/or in structure and/or in spacing on the core. Further, the arms may be a mixture of linear and branched structures. Structures with arms of various chemical compositions and/or differing terminating groups fall within this definition.

The core material in the instant invention comprises a siloxy group directly and covalently bonded to a solid support through at least one oxygen atom on the siloxy group, preferably all three. The siloxy core group is of the formula $Si(O)_m(OH)_{3-m}$, where m is equal to the number of covalent attachments to the solid support. The remainder of the dendrimer is directly attached to the siloxy core through a single branch point on the Si atom. By directly it is meant that the dendrimer is attached to the siloxy either directly or through a small linker, preferably a linker of less than 13 carbons, more preferably n-propyl.

The supported dendrimers of the instant invention have the advantage that they are attached to particulate solid supports, which are suitable to be used under most reaction conditions. They combine the advantages of heterogeneous catalysts with their simple separation from the reaction products, with the stability of homogenous catalysts. Since the dendrimers are covalently and directly attached to the solid supports, they are less likely to be separated from the supports than catalysts attached to solid supports through indirect means or through large, bulky intermediate linkers.

The supported dendrimers of the instant invention also have the advantage that they can be easily separated from reaction solutions of all types. Unsupported dendrimers tend to have very small particle sizes, some in the order of nanometers. Separation of these dendrimers is complicated and typically requires the use of ultra-filtration techniques. Embodiments can be made with particle sizes in the range of 35–70 μm for powders, with particles suitable for fixed bed uses in the range of 5 μm to 20 mm. Separation techniques are therefore simplified. Techniques that can be used include membrane filtration for fine particles and standard filtration techniques for larger particles.

The solid support is any solid material to which the siloxy group can be covalently bound. Preferred supports are $SiO_2$, Al$_2$O$_3$, TiO$_2$, ZrO$_2$, clays, zeolites, and modified carbons, with SiO$_2$ being the most preferred. The supports may be used as is or may be surface modified.

The dendrimer arms attached to the siloxy core may consist of linear organic (aromatic or aliphatic) or inorganic oligomers or polymers. The connecting atoms can consist of any material, which can form oligomers such as carbon, silicon, phosphorous, and the like. The arms may be linear, lightly branched, highly branched, or cross-linked, and preferably at least one of the arms should contain at least one further branch and contain at least two branch points.

A preferred embodiment of the instant invention consists of a siloxy core bonded to a dendrimer via an amine functional group through an alkyl or aryl link, of the formula Si(O)$_m$(OH)$_{3-m}$[ZN], wherein m is 0–3, Z is the alkyl or aryl link, and the two starting arms of the dendrimer are attached to the N. The alkyl or aryl linkage Z is hereby defined as any optionally substituted C2–C12 straight chain or branched alkyl chain, cycloalkyl group, or aryl group. Examples include but are not limited to ethyl, n-propyl, isopropyl, n-butyl, isobutyl, tert-butyl, cyclohexyl, and phenyl. A preferred embodiment is of the formula —(CR$_1$R$_2$)(CH$_2$)$_x$—, where R$_1$ and R$_2$ are hydrogen or alkyl and x is 1–11. Most preferred is where R$_1$ and R$_2$ are H and x is 3.

One embodiment of a dendrimer in the instant invention that is directly and covalently bonded to a solid support via a siloxy core can be described as Si(O)$_m$(OH)$_{3-m}$[ZN](AB)$_g$(T)$_{2g}$ wherein Si(O)$_m$(OH)$_{3-m}$ and Z is as defined above; A is —(CHR$_3$)CHR$_4$Y—; Y is selected from the group consisting of —C(O)NH—, —P(O)(OR$_5$)NH—, and —C(N)NH—; B is —R$_6$NH—; T is selected from the group consisting of H, alkyl, —(CR$_8$R$_9$)$_y$NH$_2$, —(CR$_8$R$_9$)$_y$P(R$_{10}$)$_2$, and —(CR$_8$R$_9$)$_y$P(NH$_2$)$_2$; R$_3$, R$_5$, R$_8$, and R$_9$ are independently selected from the group consisting of hydrogen, alkyl or aryl; R$_6$ is selected from the group consisting of optionally substituted C2–C12 straight chain or branched alkyl chain, cycloalkyl group, and aryl; R$_{10}$ is selected from the group consisting of hydrogen, alkyl, aryl, alkoxy and aryloxy; m=0–3; n=0–11;x=2–12;y=1–9; and g=

$$\sum_{1}^{G} 2^G$$

where G=number of generations in the dendrimer.

A preferred embodiment is where Z is —(CH$_2$)$_3$—, A is —(CH$_2$)$_2$C(O)NH—, B is —(CH$_2$)$_2$N—, and T is —(CH$_2$)$_2$NH$_2$.

One embodiment of the dendrimer attached to the linker can be prepared via the systematic addition of a compound having at least two reactive functional sites, and a diamine. These can be prepared by any method known in the art, including but not limited to the method described in U.S. Pat. No. 4,507,466, hereby incorporated by reference.

Compounds having at least two reactive functional sites that are suitable for preparing the dendrimer of the instant invention include but are not limited to compounds of the formula HR$_3$C=CR$_4$Y, wherein Y is —C(O)OR$_{11}$, —P(O)(OR$_5$)$_2$, —CN, or —C(O)NH$_2$, and R$_3$, R$_4$, and R$_5$ are as defined above, and R$_{11}$ is selected from the group consisting of hydrogen, alkyl or aryl. A preferred compound is methyl acrylate. Diamines suitable for this procedure include but are not limited to compounds of the formula H$_2$N—(CR$_8$R$_9$)$_n$—NH$_2$, wherein R$_8$ and R$_9$ are independently hydrogen, alkyl or aryl, and n is 1–12. A preferred compound is ethylenediamine.

The dendrimers may be attached to the solid support by any method. One method is to attach the starting core group to the solid support, and then build the dendrimer using the core group as the starting point. The linker may be attached to the core group either before or after the core is attached to the solid support, and would have at least two reactive sites onto which the dendrimer arms could be attached. A preferred starting point would be the core/linker combination Si(O)$_m$(OH)$_{3-m}$[ZN], defined above. A more preferred embodiment is Si(O)$_3$[(CH$_2$)$_3$N].

Another method is to build the dendrimer upon a core group that contains functional groups suitable for direct, covalent attachment to the solid support. After the dendrimer is complete, the core group is attached to the solid support using any suitable reaction. A preferred embodiment of a core group is H$_2$N—Z—Si(OR$_{10}$)$_3$, wherein Z is as defined above and R$_{10}$ is hydrogen, alkyl or aryl. A more preferred embodiment is H$_2$N—(CH$_2$)$_3$—Si(OMe)$_3$.

An additional embodiment of the instant invention is a supported dendrimer wherein the terminal functional groups at the end of the branches are complexed to a transition metal. The amount of complexation can vary from 1 to 100% of the terminal functional groups complexed to a metal. As used herein, transition metal means any metal from atomic number 21 up to and including 82, in addition to the metals commonly known as the actinides. Preferred metals are those of Periodic Group VIII. A more preferred metal is Rh. The transition metal may contain other ligands or counterions.

The complexation can be performed using any method known to the skilled artisan. One preferred method is to dissolve a salt or complex of the desired metal in a solvent, then to add the supported dendrimer. After stirring at room temperature for the desired period of time, the complexed supported dendrimer can be isolated by filtering through a microporous filter. A preferred method uses [RhCl(CO)$_2$]$_2$ in hexane.

The present invention also provides a process for hydroformylation, comprising reacting an organic compound comprising an ethylenically unsaturated compound optionally substituted with hydrocarbyl, substituted hydrocarbyl, or a silanyl compound with a source of CO and H$_2$ in the presence of a catalyst composition formed by the complexed supported dendrimers described previously. a Representative ethylenically unsaturated compounds, which are useful in the process of this invention, and the corresponding terminal aldehyde compounds produced are shown in Scheme I, respectively, wherein like reference characters have same meaning.

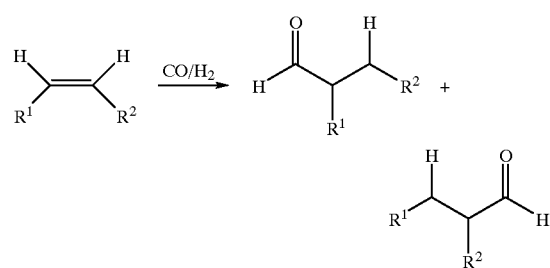

wherein R$_1$ and R$^2$ are independently H, hydrocarbyl, substituted hydrocarbyl, or silanyl.

When R$^2$ is hydrogen, the corresponding terminal aldehyde compounds can be referred to as branched or linear, as shown in Scheme II.

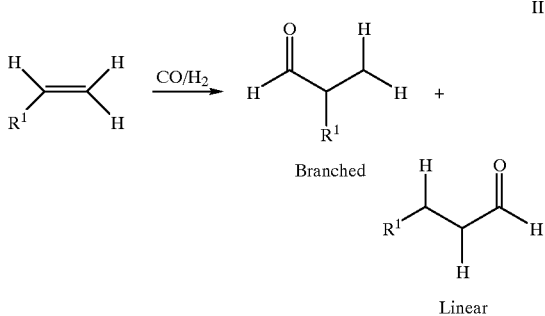

Branched

Linear

By hydrocarbyl is meant a straight chain, branched or cyclic arrangement of carbon atoms connected by single, double, or triple carbon to carbon bonds and/or by ether linkages, and substituted accordingly with hydrogen atoms. Such hydrocarbyl groups may be aliphatic and/or aromatic. Examples of hydrocarbyl groups include methyl, ethyl, propyl, isopropyl, butyl, isobutyl, t-butyl, cyclopropyl, cyclobutyl, cyclopentyl, methylcyclopentyl, cyclohexyl, methylcyclohexyl, benzyl, phenyl, o-tolyl, m-tolyl, p-tolyl, xylyl, vinyl, allyl, butenyl, cyclohexenyl, cyclooctenyl, cyclooctadienyl, and butynyl. Examples of substituted hydrocarbyl groups include acetoxy, benzoyloxy, acetyl, and pentenenitrile.

By carboxy is meant a —COOH group and derivatives thereof, such as salts and acid halides. By carboxyester it is meant an alkyl or aryl ester of a carboxy group.

Silanyl groups are hereby defined as —SiR$^3$, wherein R$^3$ is H, alkyl, aryl, alkoxy, or aryloxy. Examples of silanyl groups include trimethoxysilyl, triphenylsilyl, and triethoxysilyl.

The ethylenically unsaturated starting materials useful in this invention include unsaturated organic compounds containing from 2 to approximately 30 carbon atoms. As a practical matter, when ethylenically unsaturated compounds are used in accordance with this invention, up to about 10% by weight of the monoethylenically unsaturated compound may be present in the form of a conjugated isomer, which itself may undergo hydroformylation. Suitable unsaturated compounds include unsubstituted hydrocarbons as well as hydrocarbons substituted with groups, which do not attack the catalyst, such as cyano. These unsaturated compounds include monoethylenically unsaturated compounds containing from 2 to 30 carbons such as ethylene, propylene, 1-butene, 2-pentene, 2-hexene, 1-octene, etc.; nonconjugated diethylenically unsaturated compounds such as allene; aromatic compounds such as styrene, 4-t-butyl-styrene, 2-vinylnaphthalene, 9-vinylanthracene, and substituted compounds such as 4-methoxystyrene, allylphenylether, vinyl benzoate, vinyl acetate, 3-pentenenitrile, 4-pentenenitrile, methyl pent-3-enoate; silanyl compounds such as trimethoxysilyl and triphenylsilyl, and ethylenically unsaturated compounds having perfluoroalkyl substituents such as, for example, $C_zF_{2z+1}$, where z is an integer of up to 20. The ethylenically unsaturated compounds may also be conjugated to an ester group such as methyl pent-2-enoate.

The reaction conditions of the hydroformylation process according to this invention are in general the same as used in a conventional process, described, for example, in U.S. Pat. No. 4,769,498, hereby incorporated by reference, and will be dependent on the particular starting ethylenically unsaturated organic compound. For example, the temperature can be from room temperature to 200° C., preferably from room temperature to 150° C. The pressure may vary from atmospheric pressure to 20 MPa, preferably from 0.15 to 10 MPa and more preferably from 0.2 to 1 MPa. The pressure is, as a rule, equal to the combined hydrogen and carbon monoxide partial pressure. Extra inert gases may however be present. The molar ratio of hydrogen to carbon monoxide is generally between 10 to 1 and 1 to 10, preferably between 6 to 1 and 1 to 2.

The amount of catalyst is not specially limited, but is optionally selected so that favorable results can be obtained with respect to catalyst activity and economy.

The choice of solvent is not critical provided the solvent is not detrimental to catalyst, reactant and product. The solvent may be a mixture of reactants, such as the starting unsaturated compound, the aldehyde product and/or by-products. A preferred solvent is dichloromethane. The reaction may also be conducted with reactants and products in the gas phase.

Preferably, when a liquid reaction medium is used, the reaction mixture is agitated, such as by stirring or shaking.

For the vapor phase hydroformylation, the preferred temperature range is from about 10° C. to about 180° C. The temperature must be chosen so as to maintain all of the reactants and products in the vapor phase, but low enough to prevent deterioration of the catalyst. The particular preferred temperature depends somewhat on the catalyst and substrate being used, the olefinic compound being reacted and the desired reaction rate. The operating pressure is not particularly critical and can conveniently be from about 101.3 to 1013 kPa. The pressure and temperature combination must be chosen so that all reactants and products remain in the vapor phase.

Along with the rhodium other suitable metals may be used with the dendrimers described above to produce catalysts that may be used with other reaction types. These include hydrogenations and reductions of such groups as nitro substituted compounds, olefins, α-β unsaturated aldehydes, amides, and nitriles, reductive carbonylations, hydrocyanations, intramolecular reduction carbonylation, carbomethyoxylation, and hydrocarboxylations.

The present invention also provides a process for carbon—carbon bond formation, comprising contacting an unsaturated halide of the formula R'-X wherein X is a halogen and R' is selected from the group consisting of aryl, alkenyl and alkynyl, with a vinylic compound of the formula H$_2$C=CH—R" wherein R" is selected from the group consisting of hydrogen, hydrocarbyl, substituted hydrocarbyl, hydrocarbylamino, alkoxy, aryloxy, heterocyclic, carboxy and carboxyester, to produce a compound of the formula R'—CH=CH—R" in the presence of a Pd catalyst composition formed by the complexed supported dendrimers described previously.

The process for carbon—carbon bond formation can be, but is not limited to, the Heck reaction. The Heck reaction is a well known, very versatile reaction and any modification can be performed using the catalysts of the instant invention, including but not limited to those described in A. de Meijer, et al., Angew. Chem., Int. Ed Engl., 1994, 33, 2379. The reaction may also occur intramolecularly; that is where R' and R" are connected via substituents and form one compound, forming a ring during the reaction.

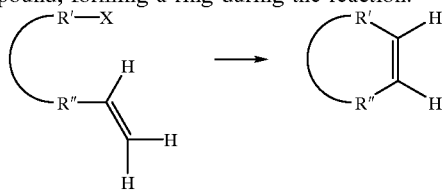

The amount of catalyst is not specially limited, but is optionally selected so that favorable results can be obtained with respect to catalyst activity and economy.

The choice of solvent is not critical provided the solvent is not detrimental to catalyst, reactant and product. The solvent may be a mixture of reactants, such as the starting Zunsaturated compound, the product and/or by-products. A preferred solvent is a dipolar aprotic solvent such as dimethylformamide.

Preferably, when a liquid reaction medium is used, the reaction mixture is agitated, such as by stirring or shaking.

A preferred version of the process of the instant invention is where R' is selected from the group consisting of aryl and substituted aryl, and R" is selected from the group consisting of carboxy, carboxy ester, aryl and substituted aryl.

The following non-limiting Examples are meant to illustrate the invention but are not intended to limit it in any way.

EXAMPLES

Example 1

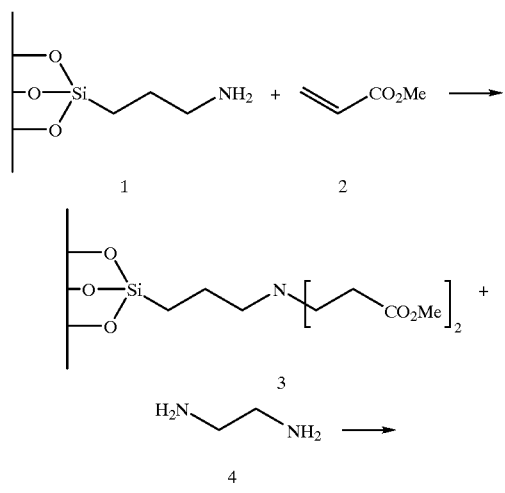

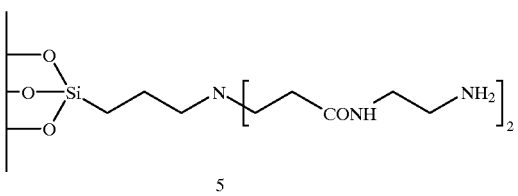

Aminopropyl silica gel (0.18 mol amino groups, 20 g, Fluka, Buchs Switzerland) and methyl acrylate (0.18 mol, 15.65 g, 99%, Aldrich, Milwaukee Wis.) were stirred together at 50° C. under nitrogen for 3 days in 100 ml of methanol (EM Science, Gibbstown, N.J.). The suspension was cooled and filtered through a medium pore frit, then washed three times each with 30 ml of methanol and 30 ml diethyl ether. Residual solvent was removed in vacuo over 24 hrs. 22.93 g of the resulting methyl gel propylaminopropionate solid (3) was isolated in 96% yield.

20 g of the resulting methyl gel propylaminopropionate (0.03 mol ester groups) and 100 ml of ethylenediamine (99%, Aldrich) in 100 ml of methanol were stirred at room temperature under nitrogen for 5 days. The resulting $1^{st}$ generation dendrimer on silica (5) was isolated by filtration, then washed with three times each with 30 ml methanol and 30 ml dichloromethane. Residual solvent was removed in vacuo over 24 hrs. 20.80 g of the dendrimer was isolated in 95% yield.

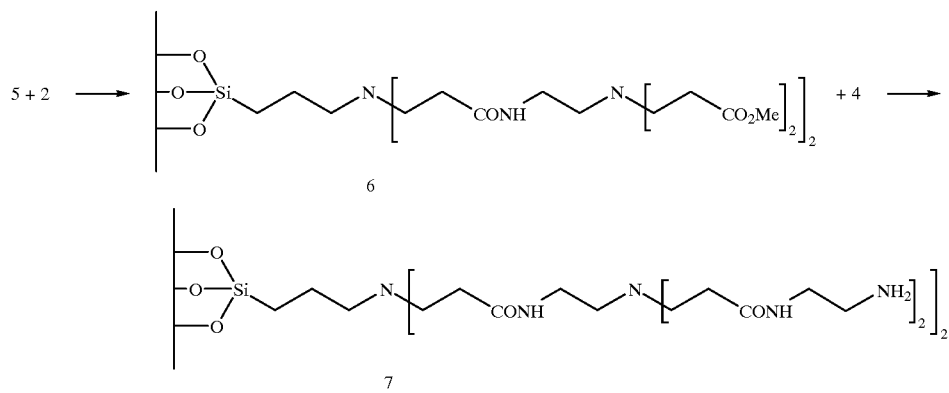

The 2$^{nd}$ generation dendrimer was prepared by reacting 20.80 g of the 1$^{st}$ generation dendrimer on silica (0.028 mol amino groups) with 0.5 mol, 43.05 g of methyl acrylate as described above, except that the reaction mixture was stirred under nitrogen for 5 days instead of 3 days. The resulting solid was then reacted after isolation with 200 ml of ethylenediamine as described above, with the exception that the reaction mixture was stirred under nitrogen for 7 days instead of 5 days. The 2$^{nd}$ generation dendrimer (7, 26.3 g) was isolated in 91% yield based on 5.

a stream of argon, and then washed with about 50 ml of degassed methanol. Residual solvent was removed in vacuo, then the resulting solid stored under argon.

60 mg of [Rh(CO)$_2$Cl]$_2$ (Pressure Chemical Co., Pittsburgh, Pa.) (0.15 mmol) was added to a solution prepared by adding 0.40 g of the phosphinated 2$^{nd}$ generation dendrimer into 20 ml of freshly distilled hexanes. The mixture was stirred at room temperature overnight under nitrogen. The resulting complexed dendrimer was filtered through a 0.45 μm membrane filter under a stream of argon,

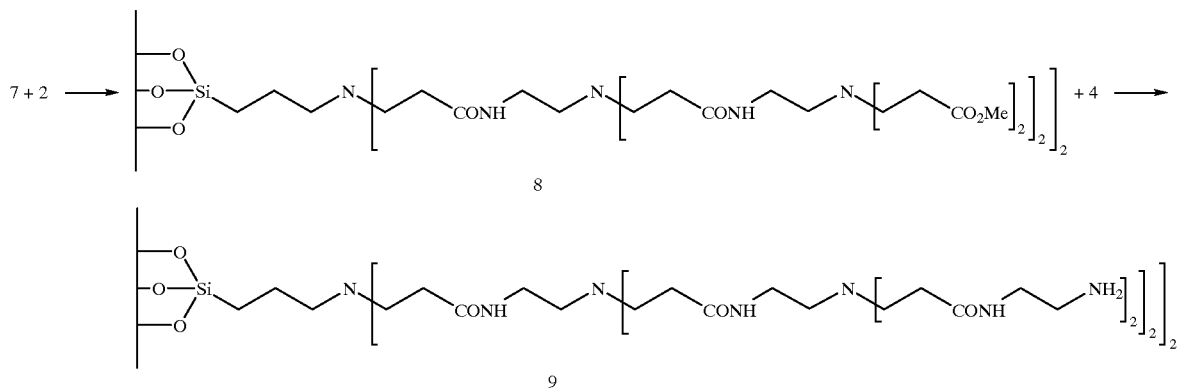

The 3$^{rd}$ generation dendrimer was prepared by reacting 26.3 g of the 2$^{nd}$ generation dendrimer on silica (0.051 mol amino groups) with 1.0 mol, 86.09 g of methyl acrylate as described for the preparation of the 2$^{nd}$ generation dendrimer. The resulting solid was then reacted after isolation with 250 ml of ethylenediamine as described above. The 3$^{rd}$ generation dendrimer (9, 36.83 g) was isolated in 94% yield based on 7.

Example 2

Omnisolve® grade methanol (EM Science, Gibbstown, N.J.) was degassed over molecular sieve (BDH 4 angstrom, 1/16 inch in pellets, Poole, Dorset BH15 1TD UK). 5.4 ml of diphenylphosphine (31.0 mmol) was added to 20 ml of the degassed methanol that contained 0.852 g (28.4 mmol) paraformaldehyde. The mixture was stirred at 70° C. for 30 min. and then cooled to room temperature. To this solution was added 0.816 g (1.82 mmol NH$_2$) of 2$^{nd}$ generation dendrimer on silica from Example 1, along with 12 ml methanol and 60 ml dried toluene. The mixture was again stirred at 70° C. for 1.5 hrs, then cooled overnight at room temperature. The resulting phosphinated dendrimer was isolated by filtration using a 0.45 μm membrane filter under and washed with 20 ml dry hexanes. Residual solvent was removed in vacua.

Examples 3–11

25 mg of the complexed phosphinated 2$^{nd}$ and 3$^{rd}$ dendrimers from Example 2 were added to glass liners that contained 2.0 mmol of an olefin in 10 ml dichloromethane. All olefins were obtained from Aldrich, Milwaukee Wis. The glass liners were then placed in an autoclave, which was charged with 500 psi of carbon monoxide and 500 psi of hydrogen, and stirred at 75° C. for 24 hrs, unless otherwise indicated. The products were filtered through a 0.45 μm membrane filter and washed with 10 ml of dichloromethane. The solvent was removed in vacuo, and the products analyzed via proton NMR (Varian Gemini 200) to determine branched liner ratio and percent conversion. Results are shown in Table 1. The catalyst used, 2$^{nd}$ or 3$^{rd}$ generation, is indicated. The 2$^{nd}$ generation catalysts were recycled and reused four times at 75° C. by washing 4 times with hexane.

TABLE 1

| Example No. | Substrate | B:L Ratio | | % Conversion | |
|---|---|---|---|---|---|
| | | 2nd | 3rd | 2nd | 3rd |
| 3 | styrene | 8:1 | 8:1 | 100 | 100 |

TABLE 1-continued

| Example No. | Substrate | B:L Ratio 2nd | B:L Ratio 3rd | % Conversion 2nd | % Conversion 3rd |
|---|---|---|---|---|---|
| 4 | 4-tert-butylstyrene | 10:1 | 8:1 | 100 | 100 |
| 5 | 4-methoxystyrene | 7:1 | 7:1 | 100 | 100 |
| 6 | 2-vinylnaphthalene | 7:1 | 7:1 | 100 | 100 |
| 7 | 9-vinylanthracene | >99:1 | — | 17 | — |
| 8 | allyl phenyl ether | 2:1 | 2:1 | 100 | 100 |
| 9 | vinyl benzoate | 19:1 | 18:1 | 100 | 100 |
| 10 | vinyl acetate | 7:1 | 9:1 | 100 | 100 |
| 11 | 1-octene | 1:2 | 1:2 | 60 | 100 |

Examples 12–13

Hydroformylations were performed with the complexed phosphinated $2^{nd}$ dendrimers using the procedure in Examples 3–11, except that the reactions were run for 72 hrs instead of 24 hrs with the temperatures indicated in Table 2. The reactions were run neat; no additional solvent was added. Complexed dendrimers were digested in HCl and HNO$_3$ using standards techniques, and then analyzed by ICP for rhodium content. Turnover numbers (TN) were calculated using the equation (mmol of product)/(mmol of Rh) (time of reaction).

TABLE 2

| Example No. | Substrate | Temp. ° C. | mmol converted | TN hr$^{-1}$ |
|---|---|---|---|---|
| 12 | styrene | 22 | 5 | 4085 |
| 13 | vinyl acetate | 35 | 10 | 8170 |

Examples 14–24

Hydroformylations were performed using the procedure in Examples 3–11, with a variety of different solvents used in place of the dichloromethane. Both the $2^{nd}$ generation complexed phosphinated dendrimer and $2^{nd}$ generation complexed unphosphinated dendrimer prepared in Example 2 were used. NMR was again used to determine % conversion and branched:linear ratio. Results on a variety of olefins are shown in Table 3.

The catalyst used was recycled in some of the examples, as indicated. Recycling was performed by rinsing with dry hexanes before reuse.

TABLE 3

| Example No. | Catalyst | Olefin | Solvent | B:L Ratio | % Conversion | Recycling |
|---|---|---|---|---|---|---|
| 14 | U | (MeO)₃Si-vinyl | Benzene | 100:0 | 100 | — |
| 15 | U | Ph₃Si-vinyl | Benzene | 88:12 | 24 | — |
| 16 | U | styrene | THF | 90:10 | 90 | 1 |
| 17 | U | styrene | $CH_2Cl_2$ | 94:6 | 100 | 2 |
| 18 | P | (MeO)₃Si-vinyl | Benzene | 76:24 | 100 | 1 |
| 19 | P | (MeO)₃Si-vinyl | Benzene | 63:37 | 62 | 2 |
| 20 | P | (MeO)₃Si-vinyl | Benzene | 70:30 | 75 | 3 |
| 21 | P | (MeO)₃Si-vinyl | THF | 48:52 | 100 | 1 |
| 22 | P | (MeO)₃Si-vinyl | THF | 58:42 | 100 | 2 |
| 23 | P | styrene | $CH_2Cl_2$ | 92:8 | 100 | 1 |
| 24 | P | styrene | $CH_2Cl_2$ | 90:10 | 100 | 2 |

U = Unphosphinated dendrimer complex
P = Phosphinated dendrimer complex

Examples 25–36

Hydroformylations were performed using the procedure in Examples 3–11, except that the temperature varied as shown in Table 4. All reaction times were 24 hrs unless shown otherwise. The catalyst used was either $2^{nd}$ or $3^{rd}$ generation complexed phosphinated dendrimer.

TABLE 4

| Ex. No. | Olefin | Temp. °C. | | B:L Ratio 2nd Gen | B:L Ratio 3rd Gen | % Conversion 2nd Gen | % Conversion 3rd Gen |
|---|---|---|---|---|---|---|---|
| 25 | styrene | 75 | | 8:1 | 8:1 | 100 | 100 |
| 26 | | 65 | | 13:1 | 13:1 | 100 | 100 |
| 27 | | 45 | | 13:1 | — | 100 | — |
| 28 | | 22 | | 25:1–30:1 | — | 100 | — |
| 29 | | 5 | 36 h | All branched | — | 5 | — |
| 30 | vinyl acetate | 75 | | 7:1 | 9:1 | 100 | 100 |
| 31 | | 65 | | — | 12:1 | — | 100 |
| 32 | | 35 | | 18:1 | 18:1 | 93 | 46 |
| 33 | | 22 | 24 h | 18:1–20:1 | — | 26–52 | — |
| 34 | | | 48 h | 17:1 | ND | 95 | 20 |
| 35 | vinyl benzoate | 75 | | 19:1 | 18:1 | 100 | 100 |
| 36 | | 22 | | 21:1 | ND | 29 | 3 |

ND = Not determined

Example 37

0, $1^{st}$, and $2^{nd}$ generation dendrimers were constructed on the surface of a silica gel particle (35–70 mm) as described in Example 1. The dendrimers on silica were phosphonated in order to provide a coordination site for palladium. Double phosphinomethylation of each terminal amine moiety was carried out using diphenylphosphinomethanol prepared in situ from paraformaldehyde and diphenophosphine as described in Example 2.

A palladium complex was synthesized starting from palladium chloride, in situ formation of the bis(acetonitrile) palladium dichloride, as described in W. de Graff, et. al, *Oranometallics*, 1989, 8, 2907, followed by displacement of the acetonitrile ligands with TMEDA (N,N,N',N',-tetramethylethylenediamine). Reaction of this complex with methyl lithium gives the Pd(Me)$_2$(TMEDA) complex shown below in 65% overall yield.

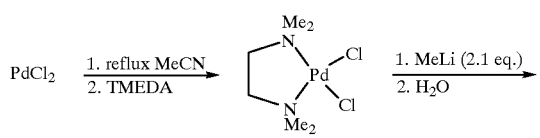

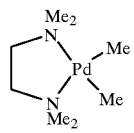

The palladium complex was complexed to the dendrimer on silica by stirring the dendrimer (1.0 mmol w.r.t PPh$_2$) in 20 ml degassed, freshly distilled benzene with one equivalent of the palladium complex (0.5 mmol), relative to the theoretical number of end phosphine groups for the respective dendrimer. The mixture was stirred at room temperature overnight under nitrogen. The product was filtered through a 0.45 μm membrane filter under a stream of nitrogen and washed with ether (50 ml). Residual ether was removed in vacuo. The complexed dendrimers were characterized by $^{31}$P solid state NMR (complexed δ=6 ppm, uncomplexed δ=−27 ppm) which indicated that the TMEDA group complexed to the Pd had been displaced by the diphenylphosphine groups on the dendrimer.

These palladium complexed PPh$_2$-PAMAM-SiO$_2$ dendrimers were digested with hydrofluoric acid or Aqua-Regia by microwave heating and analyzed for Pd content by ICP analysis. The palladium content of the various generations is summarized in Table 5.

TABLE 5

Palladium Content of PPh₂-PAMAM-SiO₂ Dendrimers.

| Dendrimer Generation | Palladium (%)[a] | gPd/gSi | $\mu$molPd/25 mg SiO$_2$ |
|---|---|---|---|
| G-0 | 2.93 | 0.0293 | 6.91 |
| G-1 | 1.34 | 0.0134 | 3.16 |
| G-2 | 1.13 | 0.0113 | 2.66 |

[a]Determined by ICP analysis

Example 38

Dimethylformamide (Aldrich) was used in anhydrous form. All the aryl bromides, iodobenzene and alkene substrates were purified before use (Aldrich). 6.0 mmol each of styrene and bromobenzene, 6.6 mmol of NaOAc (base) were mixed with 50 ml of DMF (dimethylformamide). 20 ml of this solution was placed in a 50 ml round bottom-flask equipped with a magnetic stirring bar and condenser connected to a vacuum line. The solution was flushed five times with nitrogen using a vacuum nitrogen cycle. The catalysts prepared in Example 12, generations 0 through 4, were then added. The autoclave was placed in an oil bath and the 120° C. was reached by stirring on a hot plate. After the appropriate reaction time, the reaction was allowed to cool to room temperature. The resulting solution was filtered to remove the catalyst. The filtrate was extracted with diethyl ether (4×40 ml), and the ether extracts were washed with brine and distilled water, followed by drying over magnesium sulfate. The product, trans stilbene, was analyzed by $^1$H NMR spectroscopy and/or gas chromatography, and identified by comparison of spectral results with literature data. Results are shown in Tables 6–7 below. The yields of stilbene was significantly less when generation 3 and 4 dendrimer complexes are used as catalysts. The best turn-overs in terms of molecules of trans-stilbene formed per mol of palladium was achieved with the generation 2 catalyst.

TABLE 6

Conversions in the Heck Reaction of Styrene and Bromobenzene

| Time | G-0 | G-1 | G-2 | G-3 | G-4 |
|---|---|---|---|---|---|
| 6 hr. | 67% | 10% | 17% | — | — |
| 24 hr. | 76% | 37% | 49% | 9% | 4% |
| 48 hr. | 79% | 47% | 59% | — | — |

TABLE 7

Turnovers for Generations 0, 1 and 2 (m/m/hr)

| Dendrimer Generation | Turnovers/hr. after 6 hr. | Turnovers/hr. after 24 hr. |
|---|---|---|
| 0 | 72 | 21 |
| 1 | 31 | 30 |
| 2 | 81 | 58 |

Example 39

The effect of temperature on the Heck reaction was studied with the Generation 2 catalyst. The reaction described in Example 38 was run at varying temperatures with the results shown in Table 8 below. At lower temperature the yields were low. At temperatures above 140° C. the yield was reduced by catalyst deactivation with noticeable palladium black formation.

TABLE 8

Conversions in the Heck Reaction of Styrene and Bromobenzene

| 25° C. | 50° C. | 80° C. | 110° C. | 140° C. | 170° C. |
|---|---|---|---|---|---|
| — | — | 5% | 69% | 44% | — |

Example 40

The reaction of Example 38 was repeated with the Generation 2 catalyst using the inorganic bases potassium carbonate and sodium acetate and the organic base triethylamine to determine the effect of the base on the reaction in terms of yield and recoverability of the catalyst. Results are shown in Table 9 below. Potassium carbonate and sodium acetate gave the best yields, and low product yield was found using triethylamine. system.

TABLE 9

Conversions in the Heck Reaction of Styrene and Bromobenzene

| Base | Yield of 1st run | Yield of 2nd run |
|---|---|---|
| K$_2$CO$_3$ | 53% | 43% |
| NEt$_3$ | 5% | — |
| NaOAc | 39–69% | 20–45% |

Example 41

The possibility of leaching of the catalyst into the reaction mixture was determined. The reaction of Example 38 was carried out using the G-2 catalyst, and after 16 h, the reaction was filtered under nitrogen. A further 2 mmol of styrene and bromobenzene was added and sample was taken for GC analysis. The reaction was run for a further 48 h and no further reaction of the mixture took place.

Examples 42–49

The generality of the catalytic system was investigated for a variety of haloarenes, and the results are presented in Table 10. The reaction of Example 38 was followed using the G-2 catalyst. 2.0 mmol each of the reactants and 2.2 mmol of NaOAc were mixed with 50 ml of DMF, and allowed to react at 120° C. for 48 hrs. Yields were determined by NMR analysis. It was found that the reaction of bromo and iodobenzene gave similar yields with no detectable product using chlorobenzene. Electron withdrawing substituents (nitro, ester) gave relatively low yields and conversions, while electron donating groups (methoxy, methyl) gave moderate to good yields of coupled products. The catalyst system was also found to be active for thiophenes with no catalyst poisoning resulting from the sulfur atom.

TABLE 10

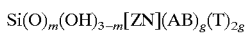

| Ex. | S¹ | S² | Isolated yield of $S^3=C(O)O^nBu$ (%) | Isolated yield $S^3=Ph$ (%) |
|---|---|---|---|---|
| 42 | I | H | — | 68% |
| 43 | Br | H | 85% | 69% |
| 44 | Cl | H | — | 0% |
| 45 | Br | Me | 76% | 81% |
| 46 | Br | OMe | 75% | 85% |
| 47 | Br | C(O)OMe | 61% | 59% |
| 48 | Br | NO₂ | 45% | 31% |
| 49 | Br | 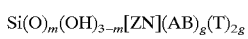 | 67% | 76% |

The invention may be varied in any number of ways as would be apparent to a person skilled in the art and all obvious equivalents and the like are meant to fall within the scope of this description and claims. The description is meant to serve as a guide to interpret the claims and not to limit them unnecessarily.

We claim:

1. A supported dendrimer composition comprising a siloxy core and branches emanating from the core, wherein said core is directly and covalently bonded to a solid support.

2. The supported dendrimer composition as in claim 1 wherein the solid support is selected from the group consisting of $SiO_2$, $TiO_2$, $Al_2O_3$, $ZrO_2$, clays, zeolites, modified carbons, and organic resins.

3. The supported dendrimer composition as in claim 2 wherein the siloxy core and branches are of the formula $$Si(O)_m(OH)_{3-m}[ZN](AB)_g(T)_{2g}$$

wherein:
Z is selected from the group consisting of optionally substituted C2–C12 straight chain or branched alkyl chain, cycloalkyl group, and aryl;
A is —(CHR₃)CHR₄Y—;
Y is selected from the group consisting of —C(O)NH—, —P(O)(OR₅)NH—, and —C(N)NH—;
B is —R₆NH—;
T is selected from the group consisting of H, alkyl, —(CR₈R₉)ᵧNH₂, —(CR₈R₉)ᵧP(R₁₀)₂, and —(CR₈R₉)ᵧP(NH)₂,
R₃, R₄, R₅, R₈, and R₉ are independently selected from the group consisting of hydrogen, alkyl or aryl;
R₆ is selected from the group consisting of optionally substituted C2–C12 straight chain or branched alkyl chain, cycloalkyl group, and aryl;
R₁₀ is selected from the group consisting of hydrogen, alkyl, aryl, alkoxy and aryloxy;
m=0–3;
y=2–12; and $$g = \sum_1^G 2^G$$

where G=number of generations in the dendrimer.

4. The supported dendrimer composition as in claim 3 wherein:
Z is —(CR₁R₂)(CH₂)ₓ—, where R₁ and R₂ are hydrogen or alkyl and x is 1–11;
A is —C(O)NH; and
T is —(CR₈R₉)ᵧNH₂, where R₈ and R₉ are independently selected from the group consisting of hydrogen, alkyl or aryl.

5. The supported dendrimer composition as in claim 4 wherein the solid support is $SiO_2$, Z is —(CH₂)₃—, A is —(CH₂)₂C(O)NH—, B is —(CH₂)₂N—, and T is —(CH₂)₂NH₂.

6. The supported dendrimer composition as in claim 3 wherein the dendrimer is complexed at T with a transition metal.

7. The supported dendrimer composition as in claim 6 wherein Z is —(CH₂)₃—, A is —(CH₂)₂C(O)NH—, B is —(CH₂)₂N—, T is —(CH₂)₂NH₂, the solid support is $SiO_2$, and the transition metal is Rh.

8. A process for the preparation of a dendrimer composition supported on a solid support comprising the steps of:
a. directly attaching a siloxy core group to the solid support by covalent bonding between at least one oxygen on the siloxy group and the surface of the solid support;
b. directly attaching a linker group to the core group, wherein the linker molecule contains at least two reactive functional groups; and
c. constructing the arms of the dendrimer utilizing the core group as the starting point of the dendrimer.

9. A process for the preparation of a supported dendrimer composition, wherein a siloxy core is directly and covalently bounded to a solid support comprising the steps of:
a. constructing the arms of the dendrimer utilizing a core group as the starting point of the dendrimer, wherein the core group is attached via a linker group to a siloxy core group; and
b. directly attaching the siloxy group to the solid support via covalent bonding between at least one oxygen on the siloxy group and the surface of the solid support.

10. The process as in claim 8 or 9 wherein the solid support is selected from the group consisting of $SiO_2$, $TiO_2$, $Al_2O_3$, $ZrO_2$, clays, zeolites, modified carbons, and organic resins.

11. A process as in claim 10 wherein said supported dendrimer composition is of the formula $$Si(O)_m(OH)_{3-m}[ZN](AB)_g(T)_{2g}$$

wherein:
Z is selected from the group consisting of optionally substituted C2–C12 straight chain or branched alkyl chain, cycloalkyl group, and aryl;
A is —(CHR₃)CHR₄Y—;
Y is selected from the group consisting of —C(O)NH—, —P(O)(OR₅)NH—, and —C(N)NH—;
B is —R₆NH—;
T is selected from the group consisting of H, alkyl, —(CR₈R₉)ᵧNH₂, —(CR₈R₉)ᵧP(R₁₀)₂, and —(CR₈R₉)ᵧP(NH)₂, $R_3$, $R_4$, $R_5$, $R_8$, and $R_9$ are independently selected from the group consisting of hydrogen, alkyl or aryl;

$R_6$ is selected from the group consisting of optionally substituted C2–C12 straight chain or branched alkyl chain, cycloalkyl group, and aryl;

$R_{10}$ is selected from the group consisting of hydrogen, alkyl, aryl, alkoxy and aryloxy;

m=0–3;

y=2–12; and $$g = \sum_1^G 2^G$$

where G=number of generations in the dendrimer.

12. The process as in claim 11 wherein the solid support is $SiO_2$, Z is —$(CH_2)_3$—, A is —$(CH_2)_2C(O)NH$—, B is —$(CH_2)_2N$—, and T is —$(CH_2)_2NH_2$.

13. The process as in claim 12 wherein the supported dendrimer composition is complexed at T with a transition metal.

14. The process as in claim 13 wherein Z is —$(CH_2)_3$—, A is —$(CH_2)_2C(O)NH$—, B is —$(CH_2)_2N$—, T is —$(CH_2)_2NH_2$, the solid support is $SiO_2$, and the transition metal is Rh.

15. A hydroformylation process comprising reacting an ethylenically unsaturated compound with a source of CO and $H_2$ in the presence of a supported catalyst, wherein the supported catalyst is a supported dendrimer composition comprising a siloxy core and branches emanating from the core, wherein said core is directly and covalently bonded to a solid support.

16. The process as in claim 15 wherein the solid support is selected from the group consisting of $SiO_2$, $TiO_2$, $Al_2O_3$, $ZrO_2$, clays, zeolites, modified carbons, and organic resins.

17. The process as in claim 16 wherein said supported dendrimer composition is of the formula $Si(O)_m(OH)_{3-m}[ZN](AB)_g(T)_{2g}$ wherein:

Z is selected from the group consisting of optionally substituted C2–C12 straight chain or branched alkyl chain, cycloalkyl group, and aryl;

A is —$(CHR_3)CHR_4Y$—;

Y is selected from the group consisting of —C(O)NH—, —P(O)(OR_5)NH—, and —C(N)NH—;

B is —$R_6NH$—;

T is selected from the group consisting of H, alkyl, —$(CR_8R_9)_yNH_2$, —$(CR_8R_9)_yP(R_{10})_2$, and —$(CR_8R_9)_yP(NH)_2$, $R_3$, $R_4$, $R_5$, $R_8$, and $R_9$ are independently selected from the group consisting of hydrogen, alkyl or aryl;

$R_6$ is selected from the group consisting of optionally substituted C2–C12 straight chain or branched alkyl chain, cycloalkyl group, and aryl;

$R_{10}$ is selected from the group consisting of hydrogen, alkyl, aryl, alkoxy and aryloxy;

m=0–3;

y=2–12; and $$g = \sum_1^G 2^G$$

where G=number of generations in the dendrimer.

18. The process as in claim 17 wherein the solid support is $SiO_2$, Z is —$(CH_2)_3$—, A is —$(CH_2)_2C(O)NH$—, B is —$(CH_2)_2N$—, and T is —$(CH_2)_2NH_2$.

19. The process as in claim 18 wherein the supported dendrimer composition is complexed at T with a transition metal.

20. The process as in claim 19 wherein Z is —$(CH_2)_3$—, A is —$(CH_2)_2C(O)NH$—, B is —$(CH_2)_2N$—, T is —$(CH_2)_2NH_2$, the solid support is $SiO_2$, and the transition metal is Rh.

21. A process for carbon—carbon bond formation comprising contacting an unsaturated halide of the formula R'—X wherein X is a halogen and R' is selected from the group consisting of aryl, alkenyl and alkynyl, with a vinylic compound of the formula $H_2C=CH$—R" wherein R" is selected from the group consisting of hydrogen, hydrocarbyl, substituted hydrocarbyl, hydrocarbylamino, alkoxy, aryloxy, heterocyclic, carboxy and carboxyester, to produce a compound of the formula R'—CH=CH—R" in the presence of a supported Pd catalyst, wherein the supported catalyst comprises a supported dendrimer composition comprising a siloxy core and branches emanating from the core, wherein said core is directly and covalently bonded to a solid; and optionally wherein the Heck reaction is performed intramolecularly resulting in a cyclic compound where R' and R" together form a ring.

22. The process as in claim 21 wherein the solid support is selected from the group consisting of $SiO_2$, $TiO_2$, $Al_2O_3$, $ZrO_2$, clays, zeolites, modified carbons, and organic resins.

23. The process as in claim 22 wherein said supported dendrimer composition is of the formula $Si(O)_m(OH)_{3-m}[ZN](AB)_g(T)_{2g}$ wherein:

Z is selected from the group consisting of optionally substituted C2–C12 straight chain or branched alkyl chain, cycloalkyl group, and aryl;

A is —$(CHR_3)CHR_4Y$—;

Y is selected from the group consisting of —C(O)NH—, —P(O)(OR_5)NH—, and —C(N)NH—;

B is —$R_6NH$—;

T is selected from the group consisting of H, alkyl, —$(CR_8R_9)_yNH_2$. —$(CR_8R_9)_yP(R_{10})_2$, and —$(CR_8R_9)_yP(NH)_2$.

$R_3$, $R_4$, $R_5$, $R_8$, and $R_9$ are independently selected from the group consisting of hydrogen, alkyl or aryl;

$R_6$ is selected from the group consisting of optionally substituted C2–C12 straight chain or branched alkyl chain, cycloalkyl group, and aryl;

$R_{10}$ is selected from the group consisting of hydrogen, alkyl, aryl, alkoxy and aryloxy;

m=0–3;

y=2–12; and $$g = \sum_1^G 2^G$$

where G=number of generations in the dendrimer.

24. The process as in claim 23 wherein the solid support is $SiO_2$, Z is $-(CH_2)_3-$, A is $-(CH_2)_2C(O)NH-$, B is $-(CH_2)_2N-$, and T is $-(CH_2)P(C_6H_5)_2$.

25. The process as in claim 24 wherein the supported dendrimer composition is complexed at T with Pd.

26. The process as in claim 25 wherein R' is selected from the group consisting of aryl and substituted aryl, and R" is selected from the group consisting of carboxy, carboxy ester, aryl and substituted aryl.

* * * * *